United States Patent
Ying et al.

(10) Patent No.: US 7,831,449 B2
(45) Date of Patent: Nov. 9, 2010

(54) METHOD AND SYSTEM FOR EXTRACTING MEDICAL INFORMATION FOR PRESENTATION TO MEDICAL PROVIDERS ON MOBILE TERMINALS

(75) Inventors: Alan J. Ying, Durham, NC (US); William T. Lawson, Durham, NC (US); Matthew Cross, Durham, NC (US); Travis Teague, Durham, NC (US)

(73) Assignee: Thompson Reuters (Healthcare) Inc., Ann Arbor, MI (US)

( * ) Notice: Subject to any disclaimer, the term of this patent is extended or adjusted under 35 U.S.C. 154(b) by 717 days.

(21) Appl. No.: 09/776,484

(22) Filed: Feb. 2, 2001

(65) Prior Publication Data
US 2005/0065822 A1 Mar. 24, 2005

(51) Int. Cl.
*G06F 19/00* (2006.01)
(52) U.S. Cl. .............................. 705/3; 705/2; 705/14.53; 705/14.54; 705/14.56; 600/300; 707/6; 455/556.2; 345/173
(58) Field of Classification Search ............... 705/2, 705/3, 14.53, 14.54, 14.56; 600/300; 455/556.2; 345/173–179; 707/6
See application file for complete search history.

(56) References Cited

U.S. PATENT DOCUMENTS

| | | |
|---|---|---|
| 5,325,293 A | 6/1994 | Dorne |
| 5,392,390 A | 2/1995 | Crozier |
| 5,497,339 A | 3/1996 | Bernard |
| 5,543,588 A * | 8/1996 | Bisset et al. ............. 178/18.06 |
| 5,561,446 A | 10/1996 | Montlick ..................... 345/173 |
| 5,659,741 A | 8/1997 | Eberhardt |
| 5,823,948 A | 10/1998 | Ross et al. |
| 5,845,255 A | 12/1998 | Mayaud |
| 5,857,201 A | 1/1999 | Wright et al. |
| 5,867,688 A | 2/1999 | Simmon et al. |
| 5,867,821 A | 2/1999 | Ballantyne et al. ............. 705/2 |
| 5,918,603 A * | 7/1999 | Brown ........................ 128/897 |
| 5,924,074 A | 7/1999 | Evans ............................ 705/3 |
| 5,992,890 A * | 11/1999 | Simcox ..................... 283/66.1 |
| 5,995,965 A | 11/1999 | Experton |

(Continued)

FOREIGN PATENT DOCUMENTS

WO    WO-9922330    5/1999

(Continued)

OTHER PUBLICATIONS

Chesanow, N., "PDAs for Doctors: Your ticket to fast, flawless prescribing," Oct. 23, 2000, Medical Economics.*

(Continued)

*Primary Examiner*—Gerald J. O'Connor
*Assistant Examiner*—Lena Najarian
(74) *Attorney, Agent, or Firm*—Plumsea Law Group, LLC

(57) ABSTRACT

A system for providing medical providers with medical records accessible from a mobile terminal in one embodiment comprises reformatting the information in a medical record database to be used with large, ergonomic icons allowing easy transitions between pages of information in the medical record. Docking stations or wireless networks may enable the mobile terminal to access the medical records. Thus, the medical provider may have bedside access to the information in the medical records to make informed decisions about treatment regimens.

49 Claims, 10 Drawing Sheets

U.S. PATENT DOCUMENTS

| | | | |
|---|---|---|---|
| 6,000,000 A | 12/1999 | Hawkins et al. | |
| 6,067,524 A | 5/2000 | Byerly et al. | |
| 6,151,581 A | 11/2000 | Kraftson et al. | |
| 6,154,726 A | 11/2000 | Rensimer et al. | |
| 6,202,060 B1 | 3/2001 | Tran | |
| 6,298,330 B1* | 10/2001 | Gardenswartz et al. | 705/14.25 |
| 6,302,844 B1* | 10/2001 | Walker et al. | 600/300 |
| 6,308,201 B1 | 10/2001 | Pivowar et al. | |
| 6,339,410 B1* | 1/2002 | Milner et al. | 345/1.1 |
| 6,558,320 B1* | 5/2003 | Causey et al. | 600/300 |
| 6,760,720 B1* | 7/2004 | De Bellis | 707/3 |
| 6,790,178 B1* | 9/2004 | Mault et al. | 600/300 |
| 6,911,969 B1* | 6/2005 | Nelson et al. | 345/163 |
| 7,099,896 B2 | 8/2006 | Fields | |
| 7,110,955 B1 | 9/2006 | Barhnart et al. | |
| 2001/0016822 A1* | 8/2001 | Bessette | 705/3 |
| 2002/0002326 A1* | 1/2002 | Causey et al. | 600/300 |
| 2002/0004729 A1* | 1/2002 | Zak et al. | 705/3 |
| 2002/0010679 A1* | 1/2002 | Felsher | 705/51 |
| 2002/0023077 A1* | 2/2002 | Nguyen et al. | 707/1 |
| 2002/0052763 A1* | 5/2002 | Richardson | 705/3 |
| 2002/0072911 A1* | 6/2002 | Kilgore et al. | 704/270 |
| 2002/0091659 A1* | 7/2002 | Beaulieu et al. | 706/62 |
| 2002/0103832 A1* | 8/2002 | Howarth | 707/526 |
| 2002/0107433 A1* | 8/2002 | Mault | 600/300 |
| 2003/0036683 A1* | 2/2003 | Kehr et al. | 600/300 |
| 2003/0158753 A1 | 8/2003 | Bernston et al. | |
| 2003/0177408 A1 | 9/2003 | Fields et al. | |
| 2004/0078215 A1* | 4/2004 | Dahlin et al. | 705/2 |
| 2004/0138569 A1* | 7/2004 | Grunwald et al. | 600/459 |

FOREIGN PATENT DOCUMENTS

| | | |
|---|---|---|
| WO | WO 00/57339 | 9/2000 |
| WO | WO 01/69446 | 9/2001 |
| WO | WO 02063541 A2 | 8/2002 |
| WO | WO 02063541 A3 | 8/2002 |

OTHER PUBLICATIONS

Fieler, K., "Palm Reader," Sep. 29, 2000, Business Journal, vol. 15, Iss. 49, p. 21.*

"Mobile MedData is the Leading Patient Information Manager for the Palm Connected Organizer," Business Wire, Jan. 3, 2000, p. 1.*

"Nifty high tech tools make the physician's life easier," Health Management Technology, Apr. 1999, vol. 20, Iss. 3, p. 22.*

Provisional U.S. Appl. No. 60/252,872.*

Provisional U.S. Appl. No. 60/216,199.*

Provisional U.S. Appl. No. 60/223,246.*

Aronow, D. "My favorite medical records PDA," Jun. 1996, Automatic I.D. News, vol. 12, Iss. 7.*

"MedicWare Introduces Electronic Medical Records Software for the Palm OS," Jan. 3, 2000, PR Newswire.*

"Leading Mobile Computing Companies Form Industry Association," Oct. 18, 1999, Business Wire.*

"Franklin's New SmartCoder.TM. Finds Medical Codes Instantly; Updatable Electronic Book Cuts Billing Time in Doctor's Offices", *PR Newswire*, (Apr. 19, 1995).

"Oracle Brings Enterprise Data Management Capabilities to PDA and Handheld PC Platforms", *PR Newswire*, (Mar. 11, 1998).

Carpenter, John , "Handheld healthcare. (handheld PCs with Microsoft's CE OS) (includes related article on PHYSIX's PocketChart virtual charting application for handheld PCs) (Technology Information)", *Health Management Technology*, 17(13), (Dec. 1996),26(3).

Davey, Tom , "Faster, Smarter, Smaller (In time, businesses will be able to use communications devices that are small enough to fit in shirt pockets; speech-recognition products are becoming more effective)", *Information Week*, (Nov. 3, 1997),125-126.

"Canadian Application Serial No. 2,434,714, Office Action mailed Apr. 15, 2009", 3 pgs.

"International Application Serial No. PCT/US02/02043, International Preliminary Examination Report mailed Jun. 16, 2003", 6 pgs.

"International Application Serial No. PCT/US02/02043, International Search Report mailed Mar. 27, 2003", 7 pgs.

"International Application Serial No. PCT/US02/02043, Written Opinion mailed Apr. 17, 2003", 5 pgs.

* cited by examiner

METHOD AND SYSTEM FOR EXTRACTING MEDICAL INFORMATION FOR PRESENTATION TO MEDICAL PROVIDERS ON MOBILE TERMINALS

BACKGROUND OF THE INVENTION

Software Code Appendix

The present disclosure includes a compact disc appendix comprising exemplary code for the present invention. The contents of this disc are hereby incorporated by reference. Pursuant to 37 C.F.R. §1.52(e) (Sep. 8, 2000) the names of the files, their date of creation, and their sizes in bytes are set forth below:

List of Files (All Created Jan. 24, 2001):

ReadMeFirst, 2kb
Folder MCentral
    MCentral ERD, 116kb (.gif file)
    MCentral Storage.sql, 1kb
    mmd_packages_constants.sql, 1kb
    mmd_packages_dictionary.sql, 2kb
    mmd_packages_med.sql, 3kb
    mmd_packages_patient.sql, 4kb
    mmd_packages_patientupdate.sql, 3kb
    mmd_packages_result.sql, 8kb
    mmd_performance.sql, 1kb
    mmd_syn.sql, 9kb
    mmd_tables_v1.0.sql, 32kb
    mmd_views_census.sql, 2kb
    mmd_views_labs.sql, 12kb
    mmd_views_meds.sql, 1kb
    mmd_views_patient.sql, 2kb
    MMDEnableConstraints.sql, 4kb
    MMDTables.sql, 28kb
    UsersRolesPrivs.sql, 1kb
Folder MData
    Folder backups
        Folder Rsc
            Folder Resource.frk
                screens.rsrc, 147kb (RSRC file)
                vssver.scc, 1kb (SCC file)
            screens.rsrc, 0kb (RSRC file)
            screens_res.h, 26kb (H file)
            vssver.scc, 1kb (SCC file)
    MData.prc, 112kb (Palm OS 3.5 application)
    Folder MData Data Model
        Documentation.txt, 4kb
        MMD_ABG_INFO, 1KB
        MMD_CBC_INFO, 1KB
        MMD_CENSUS_INFO, 1KB
        MMD_CHANGE_INFO, 1KB
        MMD_CHEM_INFO, 1KB
        MMD_COAG_INFO, 1KB
        MMD_FLUID_INFO, 1KB
        MMD_GI_INFO, 1KB
        MMD_HEART_INFO, 1KB
        MMD_LIST_INFO, 1KB
        MMD_LKP_ACTIONCODE INFO, 1KB
        MMD_LKP_BILLCODE_INFO, 1KB
        MMD_LKP_DXCODE_INFO, 1KB
        MMD_LKP_PROCCODE_INFO, 1KB
        MMD_LYTES_INFO, 1KB
        MMD_MEDS_INFO, 1KB
        MMD_MICRO_INFO, 1KB
        MMD_MISC_INFO, 1KB
        MMD_PATH_INFO, 1KB
        MMD_PREFS_INFO, 1KB
        MMD_PT_INFO, 1KB
        MMD_PTBILLCPT_INFO, 1KB
        MMD_PTBILLEM_INFO, 1KB
        MMD_PTDATA_INFO, 1KB
        MMD_PTDX_INFO, 1KB -continued MMD_PTROUND_INFO, 1KB
        MMD_RADS_INFO, 1KB
        MMD_UA_INFO, 1KB
        vssver.scc, 1kb (SCC file)
    Folder MData_Data
        Folder MData
            TargetDataWindows.tdt, 771kb (TDT file)
            CWSettingsWindows.stg, 4kb (STG file)
Folder Obj
    MData.prc, 114kb (Palm OS 3.5 file)
    MData.prc.psym, 184kb (PSYM file)
    MData.tmp, 0kb (TMP file)
Folder Rsc
    Folder Resource.frk
        Screens.rsrc, 149kb (RSRC file)
        Vssver.scc, 1kb (SCC file)
    Screens.rsrc, 144kb (RSRC file)
    Screens_res.h, 27kb (H file)
    Vssver.scc, 1kb (SCC file)
Folder Src
    MEM_LEAK.C, 3KB
    MEM_LEAK.H, 2KB
    MmdBilling.c, 28kb
    MmdBilling.h, 1kb
    MmdCensus.c, 15kb
    MmdCensus.h, 2kb
    MmdDO.c, 3kb
    MmdDO.h, 1kb
    MmdGlob.c, 5kb
    MmdGlob.h, 5kb
    MmdHotlist.c, 55kb
    MmdHotlist.h, 3kb
    MmdMData.c, 5kb
    MmdMData.h, 2kb
    MmdMeds.c, 20kb
    MmdMeds.h, 2kb
    MmdPatient.c, 25kb
    MmdPatient.h, 1kb
    MmdPHDA.c, 12kb
    MmdPHDA.h, 1kb
    MmdScribble.c, 14kb
    MmdScribble.h, 2kb
    MmdSearch.c, 15kb
    MmdSearch.h, 3kb
    MmdTest1.c, 20kb
    MmdTest1.h, 1kb
    MmdTest3.c, 18kb
    MmdTest3.h, 2kb
    MmdUtil.c, 38kb
    MmdUtil.h, 2kb
    MmdVitals.c, 11kb
    MmdVitals.h, 1kb
    SonyChars.h, 1kb
    StuffForVs.c, 1kb
        Updt.zip, 26kb (Winzip 8.0 file)
        Vssver.scc, 1kb (SCC file)
    mData Data Dictionary, 38kb (MS Word 2000 document)
    Mdata.mcp, 41kb
    Mdata.old.mcp, 41kb
    mmdi.zip, 713kb (WinZip 8.0 Document)
    PatentApp.zip, 140kb (WinZip 8.0 Document)
    vssver.scc, 1kb
Folder Minterface
    MmdIE.cls, 24kb
    MmdMC_Ora.cls, 33kb
    MmdMed.cls, 4kb
    MmdPatient.cls, 6kb
    MmdResultGroup.cls, 3kb
    MmdResultGroupTypes.cls, 3kb
    MmdResultTypes.cls, 3kb A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

1. Field of the Invention

The present invention relates to a technique for accessing medical databases and delivering the content thereof to medical providers through a mobile terminal.

2. Description of the Related Art

Medical providers are notoriously resistant to change in their workplace. As a result, they frequently do not accept new technology simply because it is new and may not be better. Medical providers often only accept change when they have to or when it truly does make their job demonstrably easier and/or faster.

Conversely, a common complaint among many medical providers is the lack of access to information needed to treat patients effectively. Medical providers are loath to travel to an inconveniently located desktop terminal or workstation only to spend several minutes logging into the system, accessing a database, and then slowly sifting through the medical records that may be contained therein in an attempt to find a bit of desired information and then transcribing it or printing it out for later use.

Medical institutions, such as hospitals, may have a paper file with hard copies of the pertinent medical information, but again, this is cumbersome, antiquated, and not always orderly. As more hospitals move to electronic databases, even these portable, albeit outmoded, records may be hard to come by. Thus, the two primary vehicles by which medical records may be accessed are inadequate to help medical providers access the medical records where they are needed the most—by the patients' bedsides.

Let it not be said that medical providers are completely hateful of new technology. Many medical providers have become addicted to handheld devices such as the ubiquitous PALM PILOT® series of devices. Likewise, many doctors may supplement their PALMS or replace them entirely with wireless telephones and/or pagers. Such devices, collectively referred to as mobile terminals, are uniquely positioned to provide access to the medical records that the medical providers desire. However, a barrier remains in that the medical records are typically held in a proprietary database isolated from wireless access and are not in a format that is conducive to presentation on a mobile terminal.

SUMMARY OF THE INVENTION

The present invention comprises a technique to enhance patient care by providing medical providers with accurate, up to date, easily accessible information about the patients in their care presented in an ergonomic and intuitive fashion. Initially, databases of medical records, typically stored by a hospital, are accessed and the information contained therein is extracted and reformatted in a consistent manner. Software may be used to perform this extraction and reformatting. These medical records are then provided to the medical providers through a mobile terminal.

In one embodiment, the present invention provides the medical records to a personal digital assistant such as a PALM PILOT®. The display of the personal digital assistant comprises a plurality of large, ergonomic buttons that may be used to transition between different screens of information in the medical records. Medical providers synchronize to the database at regular intervals to keep the records on the personal digital assistant current as well as to update the hospital database with information entered into the personal digital assistant.

In a second embodiment, the present invention provides the medical records to a mobile phone device. The mobile phone may have buttons apart from the display by which the medical provider can again transition through different screens of information in the medical records. In this embodiment, the medical provider may download only those records that he needs as he needs them. Likewise, updates are transmitted from the mobile phone back to the database. It should be appreciated that the hospital may have a Localized Wireless Telephone System or comparable system serving the hospital campus through which the mobile phone communicates with the database.

Another aspect of the present invention is the promotion and sales associated with this service. In particular, the present invention is well adapted to provide a residual revenue stream for a service provider who implements the service at a number of locations. Thus, the service provider may initially contact hospitals and other sources of the typically proprietary databases and secure permission to access and reformat the database for use with the other aspects of the present invention. This may involve a fee being paid by the service provider to the database proprietor, or better, a fee paid by the proprietor to the service provider. The service provider may further give away a number of mobile terminals to select medical providers so as to generate interest in the service. A monthly service fee may be charged to the medical providers, much like mobile phone users pay a monthly service fee for telephone service. Further mobile terminals may be sold by the service provider or a third party as needed. Likewise, it may be possible for the service provider to partner with a mobile network provider such as Ericsson to help install Localized Wireless Telephone Systems in hospitals and the like so that the present invention may be practiced more easily in hospital environments.

Still other aspects of the present invention involve charge capture services, hospital census services, and the like, all of which may be integrated into the same interface provided to the medical providers.

DETAILED DESCRIPTION OF THE INVENTION

The present invention comprises providing medical providers with medical records in a mobile terminal so that the medical providers may access the medical records without being tied to a desktop workstation. An individual or a company, both herein referred to as a service provider, may be the moving force behind these activities. It is expected that the service provider will be a profit oriented business who also desires to see the quality of care to patients improve by the provision of the medical records to the medical providers.

Figure 1:
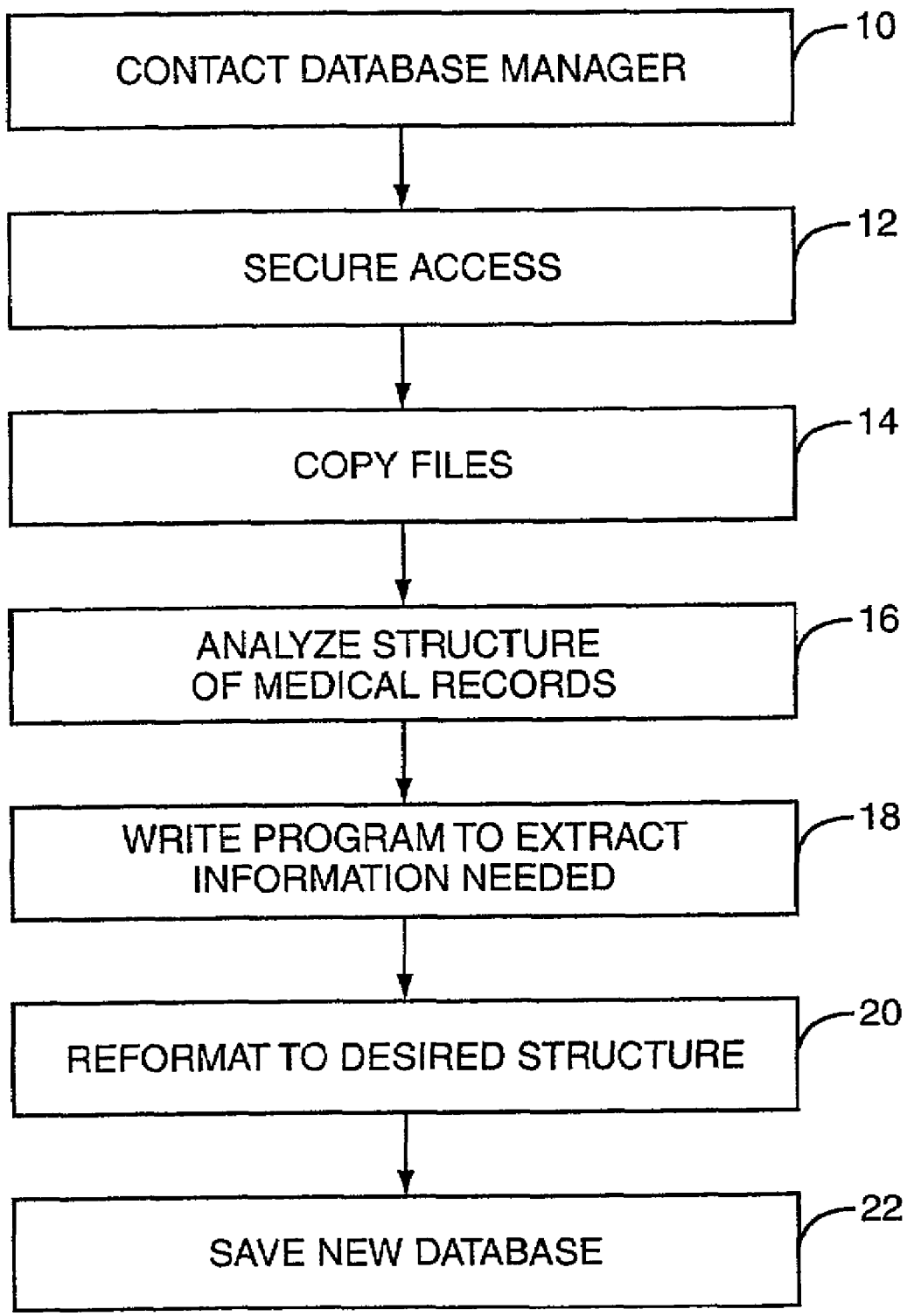
FIG. 1 illustrates a flow chart describing accessing databases for creation of the modified medical records of the present invention.

Initially, the service provider will have to acquire the medical records in a format that is amendable to presentation on the mobile terminals. A flow chart of this initial process is illustrated in FIG. 1. The service provider, or a representative of the service provider, may contact the managers of the databases containing the medical records (block 10). It is expected that these managers may be hospitals or companies to whom hospitals have outsourced the medical record maintenance responsibilities. E.g., Cerner and Shared Medical System. In some cases, these companies merely sell software to the hospitals depending on the preference of the hospital, in which case, the manager of the database may be a hospital employee. Additionally, it is possible that medical providers who are not associated with a hospital (e.g., a practice group, a partnership, a solo practitioner, or the like) may have medical records amenable to incorporation and use in the present invention. Thus, the service provider may also contact such individuals or groups and the present invention is not restricted to hospitals per se.

After the appropriate sales presentation, the database manager may pay a fee to the service provider. Alternatively, the service provider may pay a fee to the database manager. Regardless of the nature of the transaction, the service provider secures access to the database (block 12).

In one embodiment, the files are copied to a computer memory local to the service provider (block 14), leaving the original database unmodified. The medical records are analyzed for the structure thereof (block 16). Specifically, it is desired to learn what fields of the database contain what information. The service provider may then write a software program that extracts the information from the copied files (block 18) and inserts it into a new database in the format desired (block 20). The new database is then saved (block 22). This is a rather brute force approach, but is certainly possible.

In another embodiment, where the medical records only exist in a paper format, the service provider may hire data entry personnel to read the medical records and enter the desired information into the new database. This is, as would be expected, inefficient and very labor intensive, but having been done once for that particular collection of medical records may not need to be done ever again. For example, it may be appropriate when a wholesale conversion from a paper office to an electronic office is contemplated.

In yet another embodiment, the original database may communicate with the new database through standard Open DataBase Connectivity (ODBC) drivers. The service provider may then simply query the original database and derive the desired information.

In still another embodiment, the original database may be HL7 certified. HL7 stands for Health Level 7 and is a standard presently in its third version. Details may be found at www.hl7.org. In essence, this standard allows data to be passed between providers and used as desired. Either of the last two cases greatly simplifies the extraction and translation of the data from the original database to the new database created by the service provider.

Figure 2:
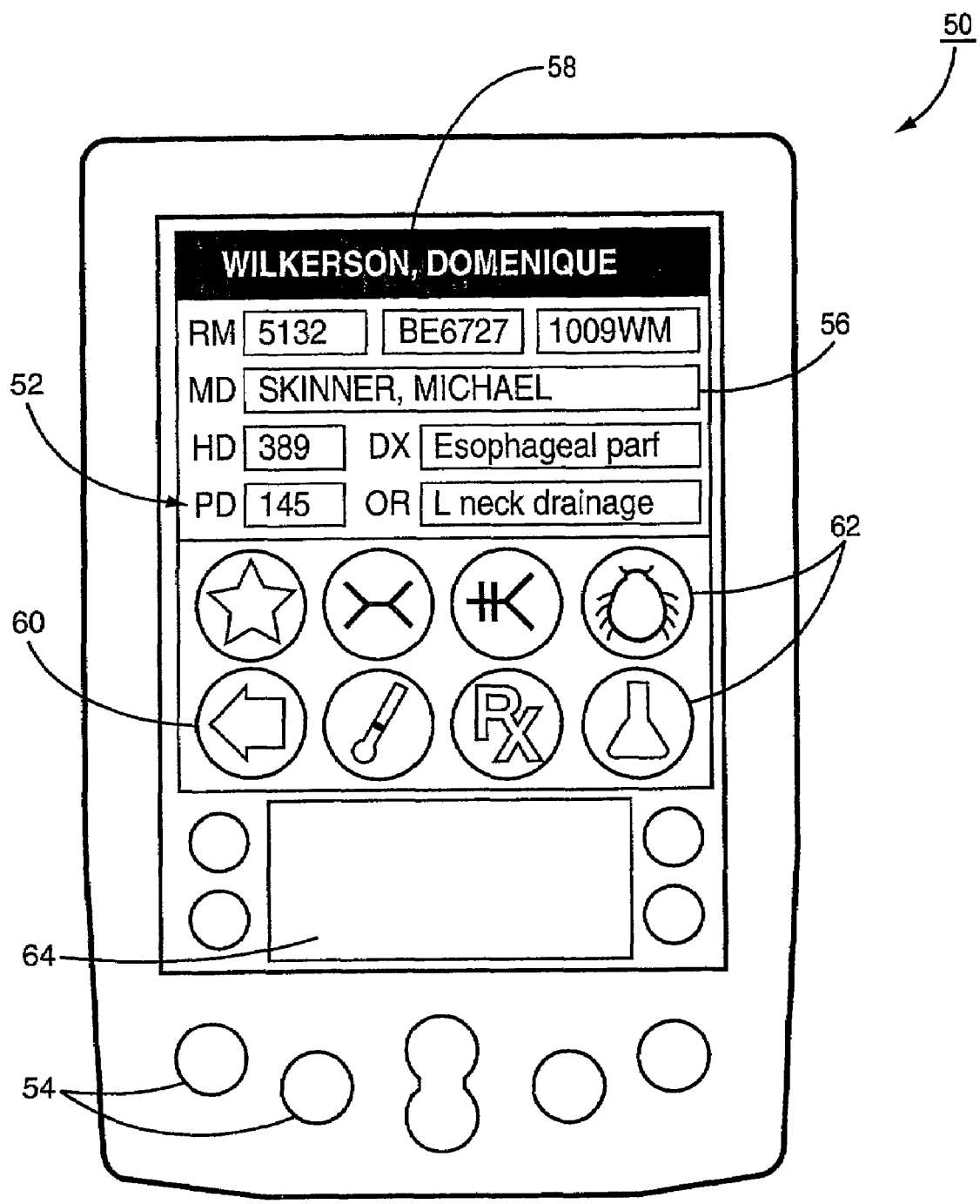
FIG. 2 illustrates a front plan view of a personal digital assistant with a medical record displayed thereon.

The purpose of the extraction and reformatting is to present the data of the medical records in a format that is acceptable for display on a mobile terminal. To facilitate an explanation of the methodology of the present invention, what follows is a discussion of the hardware. It should be appreciated that the term mobile terminal may include a cellular radiotelephone with or without a multi-line display; a Personal Communications System (PCS) terminal that may combine a cellular radiotelephone with data processing, facsimile and data communications capabilities; a PDA that can include a radiotelephone, pager, Internet/intranet access, Web browser, organizer, and/or calendar; and a conventional laptop and/or palmtop receiver or other appliance that includes a radiotelephone transceiver. Mobile terminals may also be referred to as "pervasive computing" devices. However, the present application will focus on two such devices, namely personal digital assistants (mobile terminal 50) such as that illustrated in FIG. 2 and mobile phones (mobile terminal 100) such as that illustrated in FIG. 4. Mobile terminal 50 may be a PALM PILOT® or the like and may comprise a display 52 and a plurality of buttons 54 as is conventional. Display 52 may include a data field 56 comprising a patient's name field 58, a movement icon 60 and a plurality of special icons 62. As is conventional on most personal digital assistants, display 52 may comprise some form of touch screen, accepting inputs by touching the display 52. Display 52 may further comprise a data entry field 64 used in conjunction with a stylus (not shown) as is conventional. In one embodiment, the display 52 comprises a color display with the icons and information displayed thereon colored to provide easy reading for the viewer. Movement icon 60 may change the information and icons displayed, in effect acting like a scroll bar. Movement icon 60 and special icons 62 are sized so as to be actuatable by a finger rather than a stylus and include imagery that is a convenient shorthand representing medical information. Special icons 62 are explained in greater detail below with reference to FIG. 6.

Figure 3:
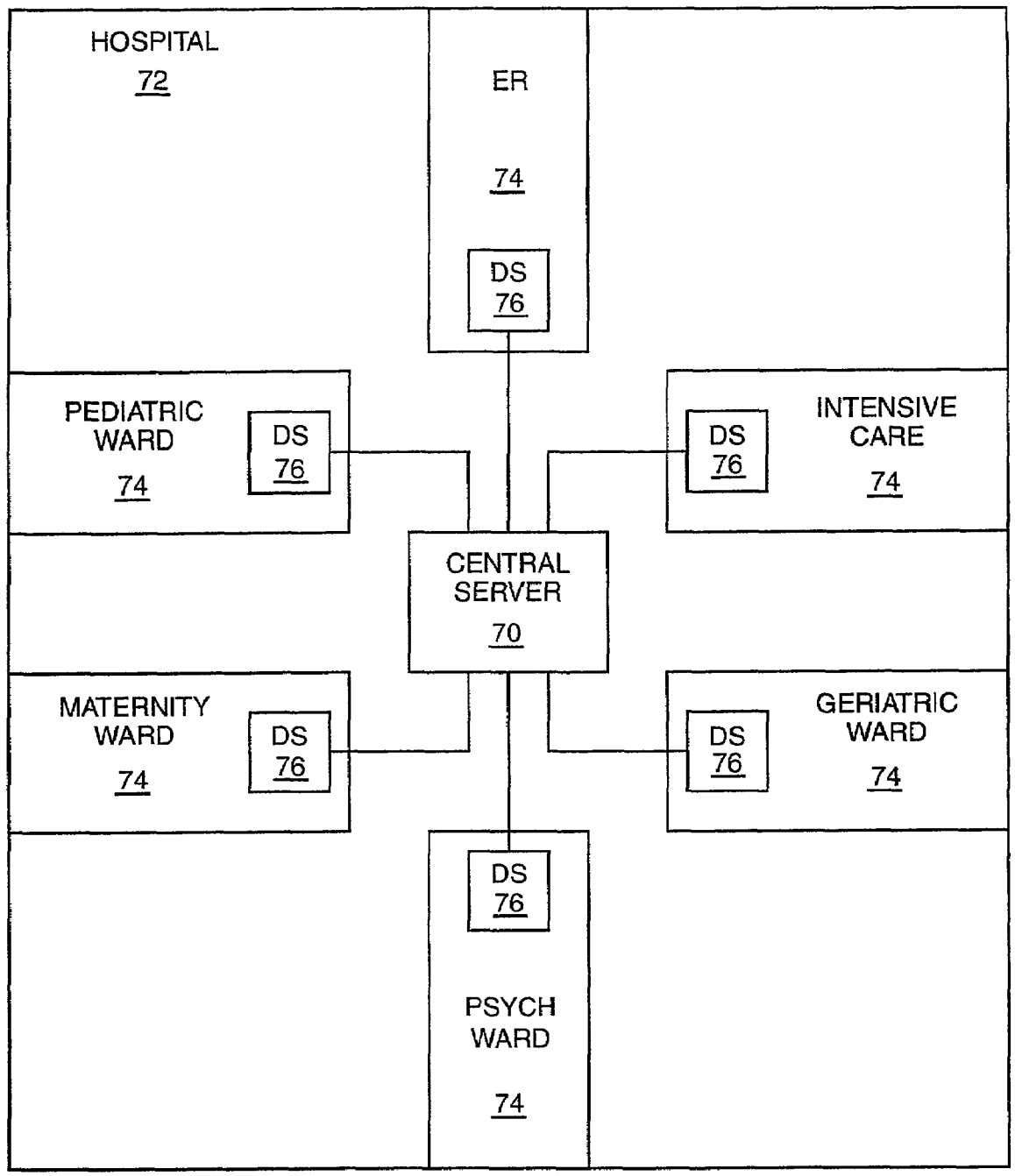
FIG. 3 illustrates a schematic diagram of a hospital with multiple docking stations for synchronization of the personal digital assistants of the present invention.

Personal digital assistants, such as mobile terminal 50 may not be equipped with long range transceivers and may require docking stations through which they receive access to the database in which the properly formatted medical records are contained. This situation is illustrated schematically in FIG. 3. In particular, a central server 70 may be positioned anywhere within the hospital 72. Central server 70 may comprise a single processor, a plurality of CPUs, or the like as needed or desired and have memory associated therewith on which the reformatted database is stored. In one embodiment, the central server 70 may be an ORACLE based server. Other servers may also be appropriate and the particular server is not material to the present invention.

Hospital 72 may include a plurality of wards or divisions 74 each with a docking station 76 communicatively connected to the central server 70. In one embodiment, the connection is provided by EXTENDED SYSTEMS' XTNDCONNECT SERVER. In practice, medical providers will periodically bring the mobile terminal 50 to one of the docking stations 76 and synchronize with the information stored on the central server 70. Docking stations 76 may require a physical connection, but are more favorably infrared transmission based, allowing synchronization of five to eight mobile terminals 50 simultaneously. An acceptable device to do this the CLARINET SYSTEMS EthIR LAN that transforms standard existing Ethernet connections to wireless access points. The EthIR Beam module supports Windows CE™, PALM™, EPOC, and LINUX devices, and is capable of 4 Mbps throughput while complying with all the appropriate IEEE, FCC and IrDA standards.

It should be appreciated that the synchronization is designed to be two-way. For example, in the morning, a medical provider docks his mobile terminal 50 in a docking station 76 and downloads information into the memory of the mobile terminal 50 related to his access privileges. As the medical provider performs his rounds, he or she enters data into the mobile terminal 50 relating to treatment regimens and the like. Upon completion of the rounds, the medical provider docks again, uploading the information entered into the mobile terminal 50 into the database for sharing with other medical providers. Note that this upload may update the information not only in the central server 70, but also in the original hospital database if it is stored in a different memory device, such as the original hospital server. This process of downloading and uploading, or synchronizing is well understood in the art.

Note that hospital 72 is used as an example, and is not intended to be limiting. Smaller facilities may not need more than one docking station 74 per building. Variations on this are well within the skill of those in the art.

Figure 4:
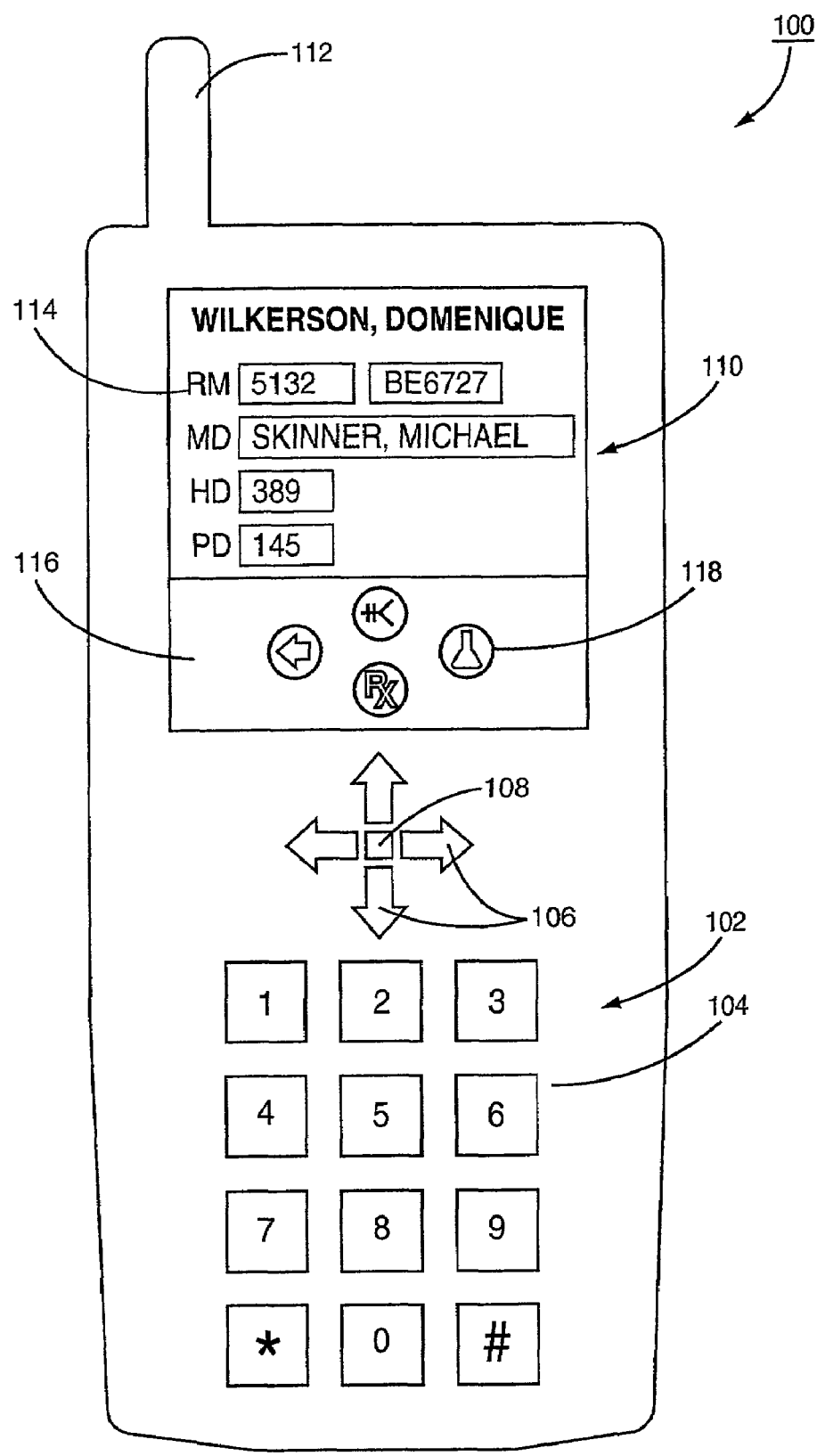
FIG. 4 illustrates a front plan view of a mobile phone with a medical record displayed thereon.

An alternate embodiment may incorporate radio frequency (RF) wireless technology wireless protocols. An exemplary mobile terminal 100 is illustrated in FIG. 4. Mobile terminal 100 may comprise a keypad 102 having numerical keys 104, directional keys 106 and a select key 108; a display 110; and an antenna 112 as is well understood in the wireless communication industry. Mobile terminal 100 may be manufactured by any one of a number of different manufacturers such as ERICSSON, NOKIA, MOTOROLA, or the like. Mobile terminal 100 may conform to such standards as TIA/EIA-136, IS-95, CDMA, AMPS, D-AMPS, BLUETOOTH or the like. The standards are well documented and a further discussion is omitted. Note further, the mobile terminal 100 may also be a wireless enabled personal digital assistant that is Bluetooth enabled, uses 802.11 standards or the like. These sorts of devices avoid the need for synchronization.

Display 110 may comprise an information section 114 and an icon section 116. Information section 114 may display information from the medical record in a format that is easy to read, adapted for the size of the display 110, and corresponding to one of the icons 118 in icon section 116. Directional keys 106 and select key 108 may be used to highlight and select different icons 118 to move between different pages of information being displayed in information section 114. In effect, the icons 118 become a menu and the keys 106, 108 allow the menu to be browsed and a desired element of the menu selected.

Figure 5:
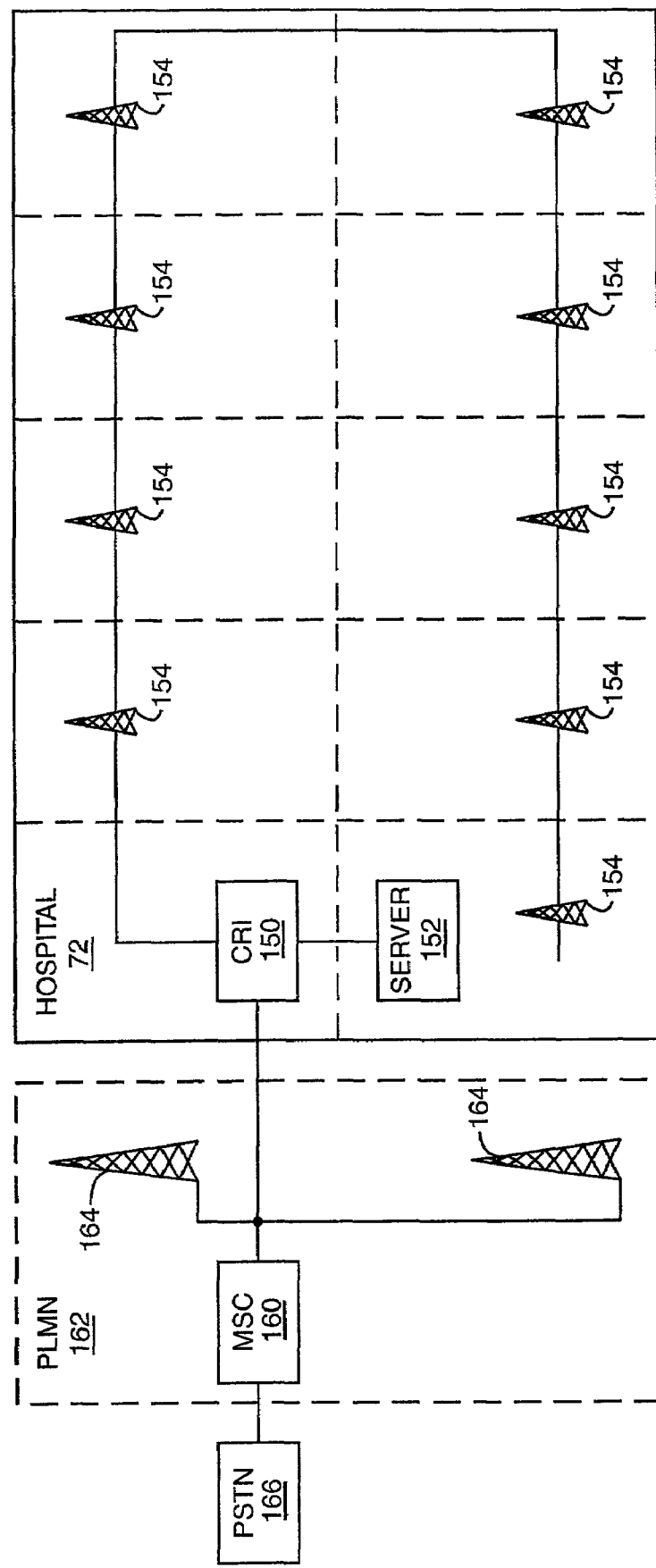
FIG. 5 illustrates a Localized Wireless Telephone System for use with the mobile phones of the present invention.

Mobile terminal 100 may be equipped with a transceiver enabling two-way communication such as is well understood in the art and as explained in the above mentioned standards. To that end, it is expected that the hospital 72 will have some sort of local, private wireless system in place to facilitate communication between a central server 152 hosting the reformatted database and the mobile terminals 100 in the possession of the medical providers. One such local wireless system is illustrated in FIG. 5. Hospital 72 may be equipped with a Control Radio Interface (CRI) 150 that is communicatively coupled to a server 152 that houses the reformatted database of the present invention, a plurality of radio heads 154, and an Mobile Switching Center (MSC) 160 within the Public Land Mobile Network (PLMN) 162. The PLMN 162 may comprise a plurality of base stations 164 as is well understood and be connected to the Public Switched Telephone Network (PSTN) 166. Suitable local wireless systems include the MOBILE ADVANTAGE™ Wireless Office sold by Ericsson, or the RBS 884 PICO SYSTEM, also sold by Ericsson. Other networks are also possible. Mobile terminals 100 may move around within the local system just like they move about in a normal cellular system. Note further that the local wireless system need not be connected to the PLMN 162 if so desired. For example, for security reasons, it may be desirable not to allow access to the PLMN 162 and the PSTN 166.

In addition to making normal phone calls, receiving pages, short message services and the like, the mobile terminals 100 may also selectively access the server 152 and secure therefrom a medical record formatted according to the present invention. It should be appreciated that appropriate encryption technology may be used so as to preserve the privacy of the medical information. The medical record is then displayed on the display 110 of the mobile terminal 100. In particular, mobile terminal 100 communicates via antenna 112 to a nearby radio head 154 and accesses server 152 through the CRI 150. The server 152 obligingly provides the requested information, which in turn is transmitted from the radio head 154 to the mobile terminal 100 for display. Any updates entered by the medical provider are forwarded upon entry by the medical provider to the server 152.

Note that servers 70, 152 may communicate with the computer containing the original, unaltered database of medical records, providing updates thereto as needed or desired. Thus, these computers may be networked through a conventional approach, selectively connected over a modem or the like as needed or desired.

As another embodiment, one in which the hospital database is used more directly, the hospital database is connected to a translator server such as an HL7 parser which in turn puts the information from the hospital database into a staging database, perhaps on the same server. The docking stations 76 or radio heads 154 then communicate with the staging database as previously described. This embodiment allows the medical providers to have access to the information in the hospital database in a more dynamic, real-time manner. This is as opposed to a one time data dump from the hospital database.

Figure 6:
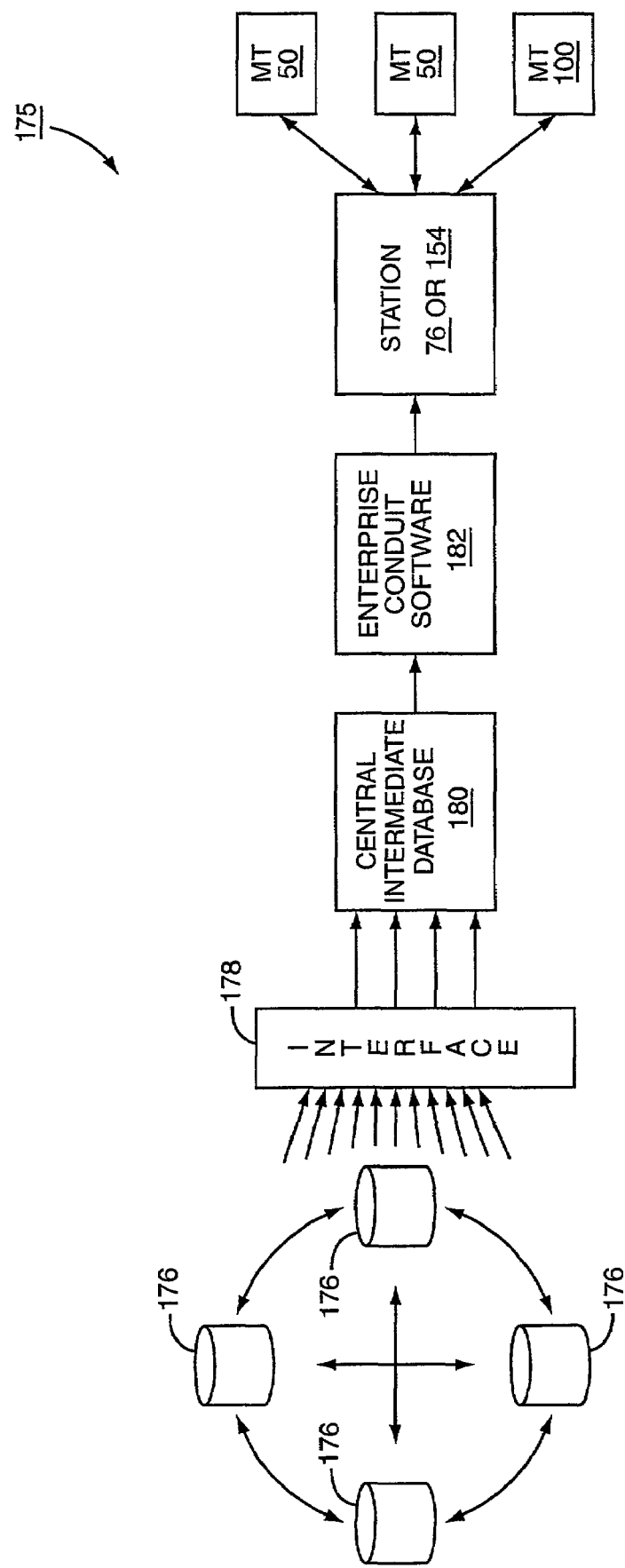
FIG. 6 illustrates a schematic overview of the database organization such as may be used in one embodiment of the present invention.

Conceptually, one embodiment of the database situation is presented in FIG. 6 noted generally at 175. Hospital databases 176 may be interconnected. An interface 178, such as any of those described above extracts the information from the hospital databases 176 and provides it to a proprietary central intermediate database 180 (this corresponds to 70 and 152). Again, this may be an ORACLE database. Enterprise conduit software 182, such as the aforementioned EXTENDED SYSTEMS' XTNDCONNECT SERVER, may be used to transport information from the central database 180 to the docking stations 76 or the radio heads 154, from which it is provided to the mobile terminals 50, 100.

Figure 7:
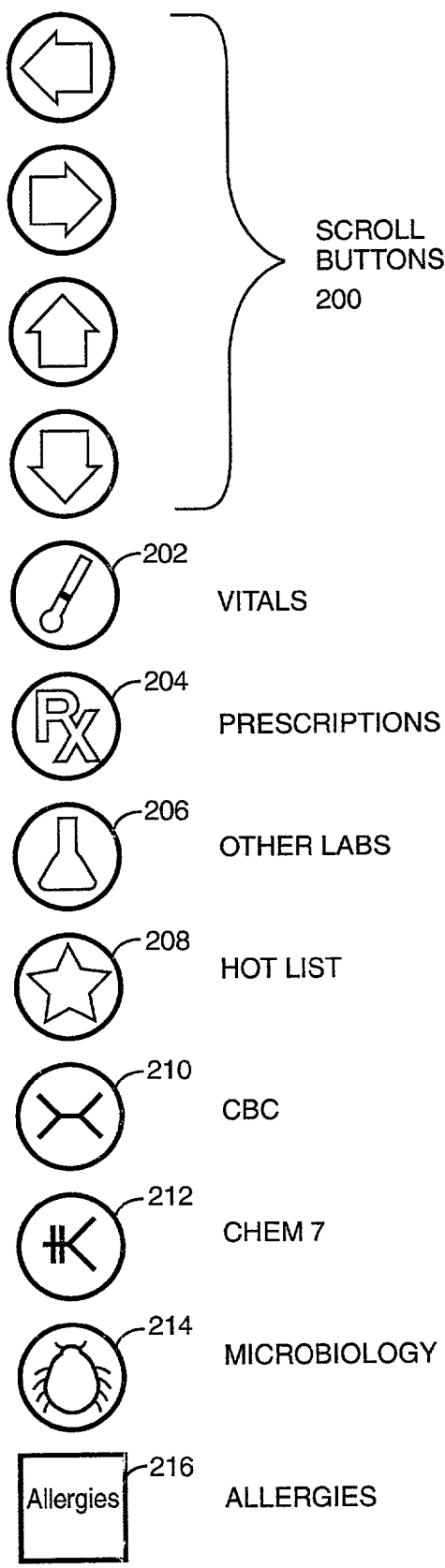
FIG. 7 illustrates an exemplary schematic chart of possible button links used with the medical records of the present invention.

Icons 118 are illustrated in tabular form in FIG. 7. Scroll icons or buttons 200 act to move medical providers between different menus or allow different icons 118 to be displayed in icon section 116. These icons may be used in place of the need for buttons on the mobile terminal 50 or 100.

Other possible icons include thermometer icon 202 that shifts the medical provider to an information screen containing information relating to the patient's vital statistics. This may be a free form data entry field to record daily events. Further, it is contemplated that the previous day's text is reproduced automatically for the next day with some indicia (such as an asterisk) that the text is reproduced. Thus, the medical provider does not have to re-enter duplicative data every day. Of course if a change is entered, this new data is displayed where appropriate.

Prescription icon 204 shifts the medical provider to an information screen containing information relating to the current medications that the patient is receiving. It may be linked to software that checks for harmful drug interactions or the like.

Other labs icon 206 shifts the medical provider to an information screen containing information relating to lab tests that may have been run for the patient. This may be presented as a pop up list that lists lab results that can then be viewed by selecting from the list. These lab tests may not be the most common sorts of tests, but are used with sufficient regularity to be included. The text of the pop up list is specifically made large enough so that the medical provider can select from the list with their finger rather than having to use a stylus.

Hotlist icon 208 shifts the medical provider to a customizable information screen. Medical providers can indicate which lab tests they desire to see most frequently. This may be related to their specialty area for example. Thus, when this button is tapped, the medical provider is taken to the tests that provide him with the most information. For example, a cardiologist may want to know the results for three certain tests, whereas an intestinal doctor may want to know the results of a different set of four tests. This icon allows the medical provider to program the mobile terminal 50 or 100 to show these desired test results.

CBC icon 210 shifts the medical provider to an information screen containing information relating to test results from a very common set of tests known as CBC.

Chem7 icon 212 shifts the medical provider to an information screen containing information related to test results from a very common set of tests known as Chem7.

Bug icon 214 shifts the medical provider to an information screen containing information related to microbiology cultures. Thus, results from cultures sent on the person are available. E.g., blood infection grew from *E. Coli*.

Allergies icon 216 shifts the medical provider to an information screen containing information related to allergies for that particular patient. It may be linked to the information in the prescription screen to check for allergic reactions to proposed medication regimens.

Other data fields include HD—the hospital day, derived from the date of admission on the hospital record; PD—post operative day; DX—diagnosis; OR—operative procedure the patient underwent; and HX—history. It is contemplated that the PD button will cause a calendar to pop up and the medical provider may indicate the day on which an operation occurred. The DX field will allow the entry of free form text so that the medical provider may indicate in their own words the patient's relevant diagnoses. Likewise, the OR field will allow the entry of free form text so that the medical provider may indicate the nature of the surgery and any other relevant details. Similarly, the HX field allows the entry of free form text about the history of the patient.

Not all of this information needs to be stored in the hospital database with the unaltered medical records. Rather, it may be stored simply in the central servers, 70, 152 and accessed by the medical providers as needed or desired. This may comprise an economically important function that allows the database to be mined for critical data that is only accessible to the end user.

The important thing about the icons is their ability to be seen easily and manipulated easily. They are preferably large enough and ergonomically designed so as to allow actuation without the need for a stylus, but rather may be actuated with a thumb or other finger. They are preferably multicolored and intuitive so that medical providers may at a glance know which icons will take them to what information. The exact placement of the icons on a display is not critical, and may be customized to the medical provider so that the icons most commonly used appear on the main screens in a desired location.

Still other commands/icons may be incorporated into the displays 52, 110. A PRINT command enables the medical provider to use infrared beaming of the patient information to an IrDA compatible printer or other comparable device.

A "Hotlist/Patient" command allows the medical provider to indicate on the preferred first screen after selecting a patient's name from a list of patients. This button is exemplary of the ergonomic innovation of the present invention in that it speeds work flow by allowing quicker access to the more relevant information that the medical providers need. This may be, for example, the hotlist test results, or a general default patient information screen having HD, PD, and OR information. Other screens are also possible as needed or desired.

A NOTE command takes the user to a totally freehand blank screen that allows the medical provider to draw notes, pictures, or the like as needed. This command in particular may be preserved in a particular position on the display 52, 110 in every screen, such as the lower right hand corner. Notes may be erased with an ERASER button on the scribble screen. Further, the contents of this screen will be linked to the patient file such that if a medical provider scribbles some notes about a patient, then switches through multiple other screens and/or patient information, upon returning to the note button for the original patient, the notes are still available for the medical provider to view. This maybe done with memory in the mobile terminal 50, 100 or in the server that stores the medical records.

A DETAILS command allows the medical provider to secure more details about a particular lab or test result. In particular, it is expected that many lab or test results will be abbreviated with the most commonly desired information presented first. Additional details will be available through the use of this command. Access to the additional details will be achieved by touching the result set of interest on the screen.

An ADD PATIENT command may be displayed as a "+" sign or the like, and allows the medical provider to enter a patient's medical record number or other unique patient identifier manually, and at the next synchronization, the patient's complete medical record will be loaded into the memory of the mobile terminal 50, 100. In the situation where the mobile terminal is a mobile type device, this command will activate a call to the central server 152 and download the information. This feature allows medical providers to acquire access to the medical records of patients that were erroneously omitted from a synchronization or added to the ward after a synchronization visit.

Other features are also possible. For example, as an alternate revenue generator, the service provider could sell advertising on a "Product of the Day" icon. This icon may likewise be ergonomically designed so that it complements the rest of the icons and is used because it is easy and intuitive. This might be located in an unobtrusive portion of the display 110 so as to avoid inadvertent triggering. Medical providers may peruse this feature in down time, such as when waiting on an elevator, eating a meal, or the like. This may eliminate needless interruptions by sales representatives or the like. Further, in one embodiment of the present invention, when medical providers subscribe to the present service, they would identify their specialty areas and qualifications. This may be done to differentiate between medical students and attending physicians, nurses, and the like. With the identification of the specialty areas, the advertising may be targeted specifically to the desired audience. For example, cholesterol drugs could be advertised to cardio-thoracic surgeons while VIAGRA™ was advertised to a geriatric specialist. In effect, this allows marksman marketing as opposed to shotgun marketing such as billboards, pamphlets, brochures, and the like. It helps ensure that the information reaches exactly the desired target audience.

As a security measure, if the mobile terminal 50, 100 is not used for an amount of time greater than a predetermined threshold, the medical provider may have to log in to the device. This may be done through any well understood user name and password type log in activity. Further, if the mobile terminal 50, 100 is not used for an amount of time greater than a second predetermined threshold, the entire memory of the mobile terminal 50, 100 may be purged of all medical records. This helps insure that access to the confidential medical information is not given to an unauthorized user.

As yet another concern, the Health Insurance Portability Account Act (HIPAA) of 1997 has laid out several federal rules about electronic data transfer as it relates to medical records. Individuals or companies who practice the present invention need to be aware of the contemporaneous interpretation of this statute to comply therewith.

Figure 8:
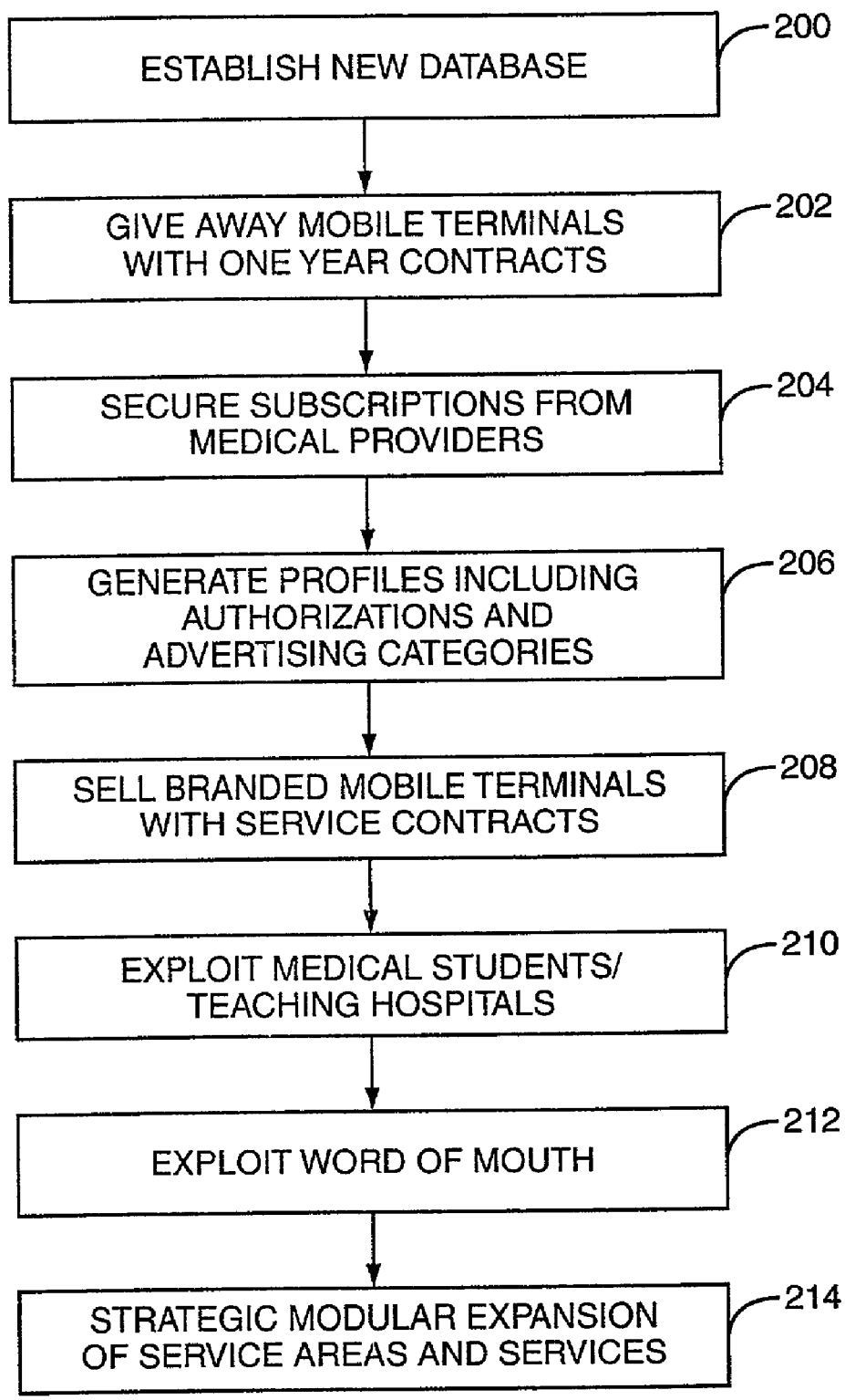
FIG. 8 illustrates a flow chart of the steps by which the present invention may be promoted to medical providers.

Against this backdrop of hardware and software, the methodology of promoting the service is presented with reference to FIG. 8. Initially, the service provider establishes the database with the information formatted in the appropriate manner (block 200). This process was described with reference to FIG. 1. The service provider may distribute for free mobile terminals 50, 100 (either personal digital assistants, mobile phones, or other appropriate device) to a select number of medical providers, for example, the first 1,000 medical providers (block 202). At the same time, the service provider could require service contract commitments from the medical providers that have just received a new mobile terminal 50, 100 (block 204). The service contract allows access to the reformatted database and any other services that the service provider provides and entails a monthly fee. Note further that the service provider may charge a monthly fee to the hospital or other entity for maintenance of the database and inclusion of new medical records. Thus, the service provider has residual revenue streams that help finance future expansions.

As part of the service contract process, the service provider may solicit information from the medical provider relating to areas of specialty and nature of their authority (block 206). For example, physicians may have different access privileges than nurses or medical students. Likewise, surgeons may need different information than a family physician who has no surgery privileges at a hospital. Other levels of access may be defined as needed.

After the initial promotional give away, the service provider may sell branded mobile terminals 50, 100 to medical providers with or without service contracts (block 208). Obviously, the service is only provided to the medical providers who subscribe to the service, but some may just desire a mobile terminal 50, 100. Discounts may be provided on the purchase price of the mobile terminals 50, 100 for those medical providers who sign long term contracts.

As an added advertising ploy, the service provider may provide mobile terminals 50, 100 and the service for free to medical students (block 210) in teaching hospitals. This exposes the medical students to the concept and utility of the service, fostering brand loyalty and occupying part of the mental desktop of the students. Then, upon graduation, the mobile terminals 50, 100 are turned in to the service provider, and the student embarks on his career. Already accustomed to the service, the new physician may demand that the hospital at which they now work invest in the service as an invaluable tool. This has worked extremely well in indoctrinating law students in the use of WESTLAW and LEXIS, resulting in a steady stream of revenue for both services. Alternatively, instead of providing the service for free, reduced rates may be provided to medical students. As yet another alternative, teachers may be encouraged to use the service during rounds with their medical students so that copies of medical records are available to all of the students simultaneously without the need for multiple paper copies.

Once a few hospitals, especially teaching hospitals begin using the service, the service provider may begin exploiting word of mouth advertising (block 212). Medical providers are generally a gregarious group, attending conferences, continuing education classes, and trade shows. Such arenas provide ample opportunity for those familiar with the service to extol its virtues to those who have not yet subscribed. These newly informed individuals may return to their establishments and demand the service. Thus, the pool of subscribers expands.

Finally, the service provider may, after reaching a critical mass of subscribers, begin embarking on strategic expansions of service areas and services provided (block 214). For example, more hospitals may be converted; small practice groups may be converted; and so on until substantially all the medical providers are using mobile terminals 50, 100 to access their medical records in an ergonomic easy to access manner. Further, in addition to just medical records, the service provider could adapt the service to include charge capture services, prescription writing services, content provision, and the like. Content provision may be Internet access along the lines of an AOL model, periodical article access, news releases about new drugs, and the like as needed or desired. These additional services may be add-ons to the basic service package, resulting in additional revenue for the service provider, or packaged together as needed or desired.

Three such packages merit further exploration as being particularly contemplated for use with the present invention. These add on features may be sold independently of the provision of medical records service, but it is contemplated that these services will be designed with similar ergonomic buttons that integrate easily into the medical record service. Medical providers using the medical record service will have at their fingertips these additional services and use them as an outgrowth of the core medical record service.

The first add-on service would be a hospital census service. Hospitals presently have a large burden in estimating patient flow through the hospital for allocating bed spaces, alerting admitting physicians as to how many beds are available for admissions and the like. This service would periodically inquire of the medical provider authorized to make a discharge of a patient when the medical provider expects to discharge the patient. Thus, the medical provider may indicate on the day after surgery that the patient is expected to stay for one week, but on the third day may indicate that the patient is healing better than expected and will be discharged the following day. This alerts the hospital to the opening of a bed space for planning purposes. The information may be stored in the same database as the medical records or separately as needed or desired. The inquiry may be through a pop up screen as when the medical provider closes a particular medical record, as an additional icon, or other technique as needed or desired.

The second add-on feature that is specifically contemplated is a feature that allows charge capture services to be implemented in conjunction with the use of the medical record. Presently, hospitals have to determine inferentially whether a service that justifies a charge has been performed. This is due in large part to the hurried nature under which many of these services are performed and the fact that the medical provider performing the service may not remember at a later time to enter the appropriate information. Thus, the service provider may include a charge capture icon or the like that inquires of the medical provider what services have been provided to a particular patient at a time relatively close to the provision of the services so as to increase the likelihood that the medical provider remembers exactly what services have been provided and thus may be billed. As an alternative to an icon, this inquiry may be in the form of a pop up window when the medical provider closes a particular record.

The third add-on feature comprises a reference interface. Selection of an appropriate icon would take the medical provider to reference material relevant to the subject about which they are concerned at the moment. These reference materials may be textbooks, the PDR, periodicals or the like. In general, periodicals may be a bit too dynamic for a synchronizing mobile terminal 50, but may be accessible by a wireless mobile terminal 100. The reference icon may take the medical provider to a dedicated search engine that only searches medical references for the desired information. Alternatively, actuating the reference icon may force the controller of the mobile terminal 50, 100 to evaluate the last command given prior to actuating the reference icon and inferentially determine what sort of resource is desired. For example, if a particular one of the Chem7 tests was being viewed in detail, and the medical provider then actuates the reference icon, the medical provider may then be provided information relevant to that test and potential diagnosis. The reference source may be provided in a HTML or WML format so that if, for example, the test states that results of X are indicative of a certain disease, the medical provider may immediately be linked to information about that disease. Other formats are also contemplated.

Figure 9:
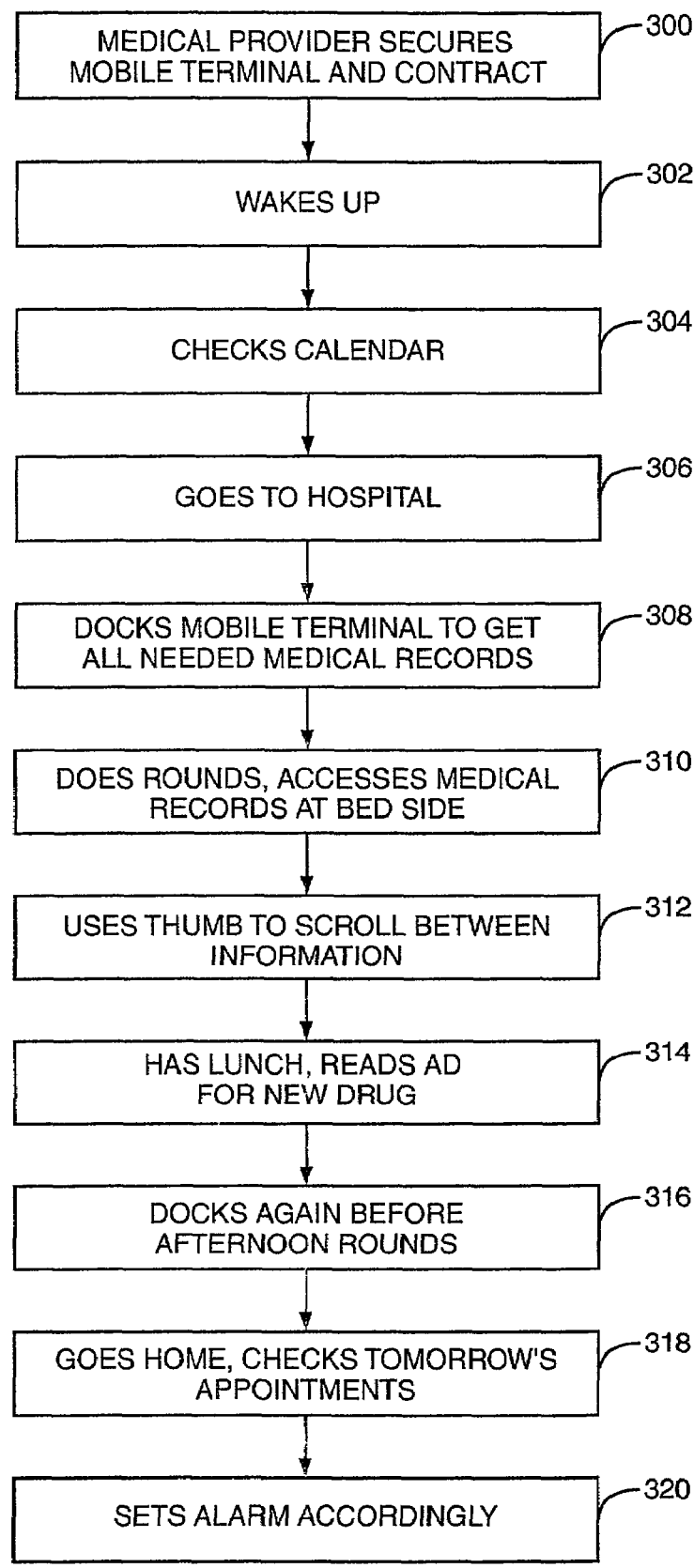
FIG. 9 illustrates a flow chart of an exemplary use session of the medical records of the present invention by a medical provider using a personal digital assistant.
Figure 10:
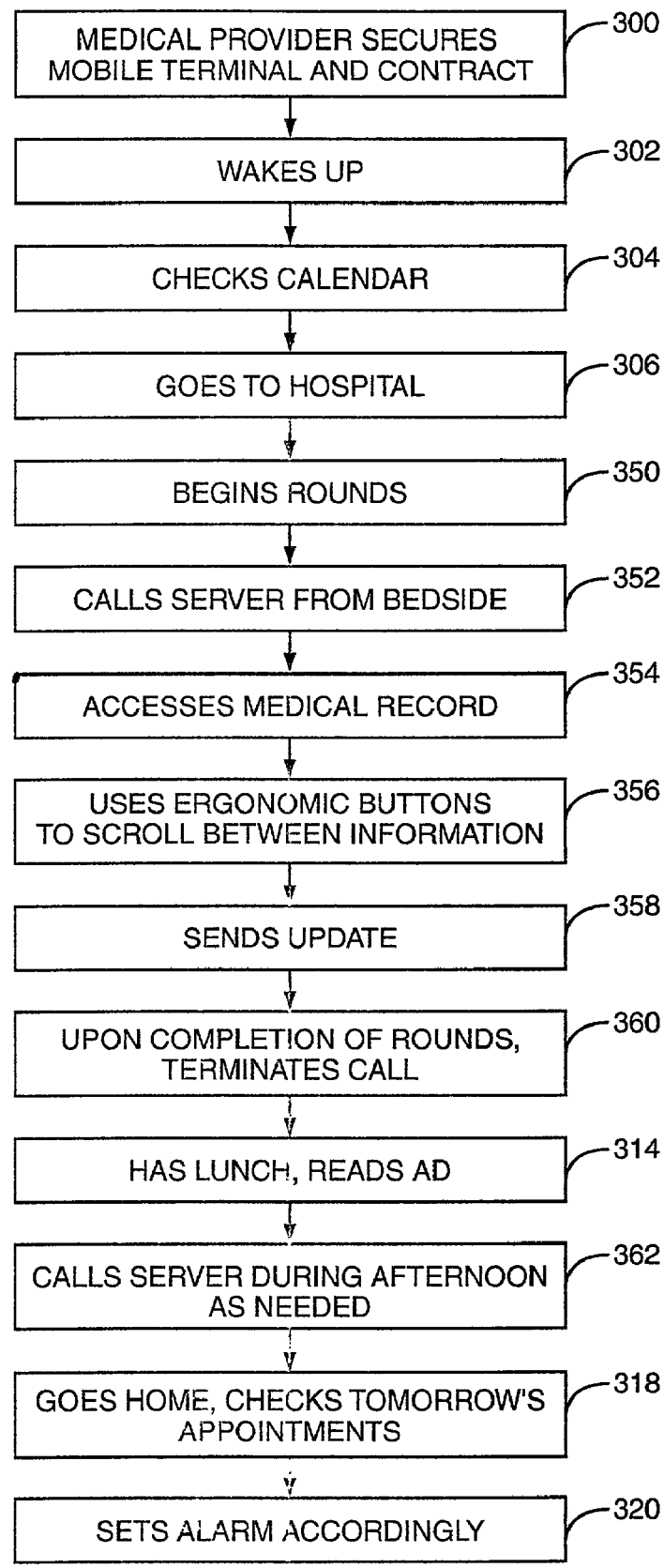
FIG. 10 illustrates a flow chart of an exemplary use session of the medical records of the present invention by a medical provider using a phone device.

Exemplary methods of using the present invention by medical providers are presented in FIGS. 9 and 10 as flow charts. These are exemplary and not intended to be limiting, but are provided to illustrate how the present invention may be used by a medical provider to make his life easier. FIG. 9 assumes that the medical provider has a personal digital assistant type mobile terminal 50. In particular, the medical provider is assumed to be a physician, although as noted above, the medical provider could in fact be a physician extender or the like such as a PA, RN, case manager, medical student or the like. The physician initially secures a mobile terminal 50 and a service contract (block 300). This may be the result of an advertising promotion, word of mouth advertising, or other reason. At some later point, the physician has begun using the personal digital assistant as a calendar and the like. The physician wakes up (block 302) and as part of his morning ritual, checks his calendar on the mobile terminal 50 (block 304) to see the day's appointments. Note that this calendar software is conventional on most personal digital assistants and is not necessarily incorporated into the software of the present invention. Both applications reside concurrently in memory on the mobile terminal 50. This may be in the midst of breakfast, between shaving and showering, or whenever is convenient.

The physician then goes to the hospital (block 306). One of the first things that the physician does is to dock his mobile terminal 50 at a docking station 76 to download all the needed medical records to the mobile terminal 50 (block 308). Note that the physician may only get medical records for his patients, the patients on the ward in which the physician works, or some other subset of all available medical records. This preserves memory in the mobile terminal 50 if desired. Some physicians may restrict access to their patients' medical records for some reason. In such a case, these may not be provided to another doctor. Of course, it is possible that every medical provider gets every medical record if so desired on the part of the service provider.

Armed with the medical records in the mobile terminal 50, the physician does his morning rounds. As part of these rounds, the physician accesses the medical records from the bedside (block 310). This allows the physician to observe the patient while reflecting on the information in the medical records. To that end, the physician may use their thumb to scroll between different screens of information in the medical record (block 312). Appropriate use of the special icons 62 and the scroll icons 60 facilitates this information access. A stylus or other data entry means may be used by the physician to enter new information into the medical record if desired.

The physician completes his rounds and has lunch. During lunch, the physician reads an ad for a new drug related to treating hemophilia (block 314). As one of the patients in an upcoming procedure is a hemophiliac, he makes a note to order some, or at least investigate further.

Before beginning his afternoon rounds, the physician docks his mobile terminal 50 again at a docking station 76 (block 316). This is done while conferring with a nurse as to the status of a particular patient about whom the physician was concerned. This docking uploads any information entered by the physician to the central server 70, while downloading any other information that has been entered since the morning docking.

After completion of the rounds, and a final docking session (not shown explicitly), the physician checks the calendar for the next day's appointments (block 318) and sets his alarm clock accordingly (block 320).

The methodology of the mobile terminal 50 is not too dissimilar from that of the methodology of the mobile terminal 100. The primary difference is the absence of the need to dock the mobile terminal. Reference is made to FIG. 10 for the methodology associated with using the mobile terminal 100. The initial part of the process is identical to that described above, namely blocks 300-306. The physician begins his rounds (block 350). Upon needing the medical record of a patient, the physician places a phone call to the server 152 (block 352). The physician then accesses the desired medical record (block 354). This phone call may be encrypted as desired to protect the privacy of the individual whose medical record is then transmitted to the mobile terminal 100 through the local, wireless telephone system. The physician uses the ergonomic buttons on the mobile terminal 100 to scroll through and select the desired screens of information (block 356).

If the physician enters new information into the medical record, the mobile terminal 100 sends the update to the central server 152 (block 358) by transmitting to a nearby radio head 154 and communicating therethrough with the central server 152. Upon completion of the physician's rounds, the physician may terminate the phone call (block 360). Again the physician may check ads during lunch (block 314). The afternoon rounds proceed substantially as the morning rounds did, with the physician placing calls to the server 152 as needed to access additional medical records (block 362). The physician's day ending routine is likewise similar (blocks 318 and 320).

While the events in the flow charts of FIGS. 9 and 10 are illustrated linearly, it should be readily apparent that the actual order of many of the events may take place as needed or desired. Life in general is nonlinear and disruptions in routine may certainly occur. Medical providers may dock more often than indicated if desired, or less frequently if desired. Further, updates may have to be entered through other means rather than through the mobile terminals 50 and 100. The flow charts are to illustrate exemplary embodiments.

The present invention may, of course, be carried out in other specific ways than those herein set forth without departing from the scope and the essential characteristics of the invention. The present embodiments are therefore to be construed in all aspects as illustrative and not restrictive and all changes coming within the meaning and equivalency range of the appended claims are intended to be embraced therein.

What is claimed is:

1. A method of presenting medical records for use by a medical provider, comprising:
    formatting medical records for electronic presentation on a display screen of a mobile terminal, wherein formatting said medical records comprises providing ergonomic actuators, electronically displayed on the display screen of the mobile terminal within said medical records, to move between different screens containing different classes of medical information regarding an associated patient, wherein each ergonomic actuator is large enough to allow actuation via a user's finger, and wherein one of the ergonomic actuators generates a customizable information screen that permits a medical provider to customize medical test results that are electronically displayed on the display screen; and further wherein activation of at least one of the ergonomic actuators causes automatic search, retrieval and display of medical reference information from a resource inferred and selected based on a type of patient test data associated with a prior user command most recently received at the mobile terminal.

2. The method of claim 1 further comprising delivering one or more of said formatted medical records to a wireless telephone.

3. The method of claim 1 further comprising delivering one or more of said formatted medical records to a personal digital assistant.

4. The method of claim 1 further comprising extracting said medical records from a hospital database prior to formatting said medical records for presentation on the mobile terminal, wherein extracting said medical records includes determining structure of the hospital database.

5. The method of claim 1 further comprising accepting input from the mobile terminal to update one or more of said medical records.

6. The method of claim 1 further comprising updating through the mobile terminal at least one of the medical records.

7. A method of presenting information to medical providers comprising:
    providing each of a plurality of medical providers with a mobile terminal;
    formatting the information to be presented in its entirety on each of the mobile terminals, wherein the formatted information includes lab result information, vital sign information, and prescription information;
    delivering the formatted information in its entirety to one or more of the mobile terminals, wherein the delivered information is associated with respective user-selectable ergonomic features that are electronically displayed on a display screen of the mobile terminal, to invoke display of the lab result information, the vital sign information, and the prescription information, and wherein activation of at least one of the ergonomic features causes automatic search, retrieval and display of medical reference information from a resource inferred and selected based on a type of patient test data associated with a prior user command most recently received at the mobile terminal, and wherein each ergonomic feature is large enough to allow actuation via a user's finger; and
    storing said reformatted medical records in a computer memory of a mobile terminal.

8. The method of claim 7 wherein providing each of a plurality of medical providers with a mobile terminal comprises initially giving at least one medical provider a mobile terminal free of charge.

9. The method of claim 8 wherein providing each of a plurality of medical providers with a mobile terminal comprises subsequently selling mobile terminals to medical providers.

10. The method of claim 7 further comprising charging a fee for access to said information.

11. The method of claim 10 wherein charging a fee for access to said information comprises charging a monthly fee for access to said information.

12. The method of claim 10 wherein charging a fee for access to said information comprises charging an annual fee for access to said information.

13. The method of claim 7 wherein delivering the information to one or more of the mobile terminals comprises delivering the information to the mobile terminals through a docking station.

14. The method of claim 7 wherein delivering the information to one or more of the mobile terminals comprises delivering the information to the mobile terminals wirelessly.

15. A method of compiling a database of medical information, comprising:
    accessing a pre-existing database of medical records;
    extracting therefrom said medical records;
    reformatting said medical records for delivery to mobile terminals and for electronic presentation on display screens of the mobile terminals, comprising providing electronic ergonomic icons on the display screens of the mobile terminals to switch display between different classes of information in the medical record, wherein each ergonomic icon is large enough to allow actuation via a user's finger, and the ergonomic icons include an icon for invoking display of lab result information, an icon for invoking display of the vital sign information, and an icon for invoking display of the prescription information, and wherein activation of at least one of the ergonomic icons causes automatic search, retrieval and display of medical reference information from a resource inferred and selected based on a type of patient test data associated with a prior user command most recently received at one of the mobile terminals; and
    storing said reformatted medical records in a computer memory of a mobile terminal.

16. The method of claim 15 further comprising updating said medical records with information provided by medical providers from mobile terminals.

17. The method of claim 16, further comprising a charge capture service to maintain a list of costs corresponding to services administered to a patient.

18. A system for delivering information to medical providers, comprising:
    a computer for storing medical records;
    a plurality of mobile terminals, wherein each mobile terminal comprises:
        a controller;
        a display operatively connected to said controller; and
        means for communicating with a database comprising medical records;

said medical records viewable on said display, said display comprising one or more electronically displayed ergonomic icons for switching between different classes of information in said medical records, wherein each ergonomic icon is large enough to allow actuation via a user's finger; and means for providing said medical records to one or more of said plurality of mobile terminals;

wherein one of the ergonomic icons generates a customizable information screen that permits a medical provider to customize medical test results that are electronically displayed on the display screen;

and further wherein activation of at least one of the ergonomic icons causes automatic search, retrieval and display of medical reference information from a resource inferred and selected based on a type of patient test data associated with a prior user command most recently received at the mobile terminal.

19. A method of providing medical records to a doctor treating patients within a medical facility, said method comprising:

providing the doctor with a mobile terminal having a memory for storing medical information regarding at least one patient;

providing a main database comprising the medical information regarding at least one patient, wherein the main database comprises a census of each patient within the medical facility and an expected discharge time;

sending the medical information regarding at least one patient from the main database to the mobile terminal and electronically displaying on the mobile terminal the medical information and pictorial ergonomic actuators that permit movement between different screens containing different classes of the medical information, wherein each ergonomic actuator is large enough to allow actuation via a user's finger;

receiving updated information from the doctor at the mobile terminal; and maintaining the main database updated by transferring said updated information from said mobile terminal to said main database;

wherein activation of at least one of the ergonomic actuators causes automatic search, retrieval and display of medical reference information from a resource infeffed and selected based on a type of patient test data associated with a prior user command most recently received at the mobile terminal.

20. The method of claim 19 wherein maintaining the main database updated by transferring said updated information from said mobile terminal to said main database comprises maintaining the main database updated by transferring said updated information from said mobile terminal to said main database through a docking station.

21. The method of claim 19 wherein maintaining the main database updated by transferring said updated information from said mobile terminal to said main database comprises maintaining the main database updated by transferring said updated information from said mobile terminal to said main database through a wireless area network.

22. The method of claim 19, further including changing the expected discharge time for a patient based on updated information from the doctor.

23. The method of claim 19 further including providing reference information to the mobile terminal upon receiving a request.

24. A method of maintaining records at a medical facility, said method comprising:

providing mobile terminals to a plurality of physicians;

maintaining a database containing a medical status of a plurality of patients;

sending information regarding at least one patient to at least one of the mobile terminals and electronically displaying on the at least one mobile terminal the information and pictorial ergonomic actuators that permit movement between different screens containing different classes of the information, wherein each ergonomic actuator is large enough to allow actuation via a user's finger, and further wherein activation of at least one of the ergonomic actuators causes automatic search, retrieval and display of medical reference information from a resource inferred and selected based on a type of patient test data associated with a prior user command most recently received at one of the mobile terminal;

receiving treatment updates from at least one of the mobile terminals; and updating the database to include the treatment updates;

wherein each of said patient's medical status comprises an expected departure date and updating the database to include treatment updates comprises altering the expected departure date; and wherein one of the ergonomic actuators generates a customizable information screen that permits a medical provider to customize medical test results that are electronically displayed on the display screen.

25. The method of claim 24, wherein each medical status comprises a bill containing each service indicated in the treatment updates.

26. A method of presenting medical records for use by a medical provider, comprising:

formatting medical records for electronic presentation on a display screen of a mobile terminal, wherein formatting said medical records comprises providing a means to move between different screens containing different classes of medical information regarding an associated patient, wherein the means does not include a stylus, a pen, a pointer, a button, or other physical device, and the means is large enough to allow actuation via a user's finger; and wherein activation of the means causes automatic search, retrieval and display of medical reference information from a resource inferred and selected based on a type of patient test data associated with a prior user command most recently received at the mobile terminal.

27. The method of claim 26, wherein the means is electronically displayed on the display screen.

28. The method of claim 26, wherein the means comprises an ergonomic actuator.

29. The method of claim 28, wherein the ergonomic actuator comprises a pictorial representation on the display screen.

30. The method of claim 1, wherein the ergonomic actuators do not include a stylus.

31. The method of claim 7, wherein the ergonomic features do not include a stylus.

32. The method of claim 15, wherein the ergonomic icons do not include a stylus.

33. The system of claim 18, wherein the ergonomic icons do not include a stylus.

34. The method of claim 19, wherein the ergonomic actuators do not include a stylus.

35. The method of claim 24, wherein the ergonomic actuators do not include a stylus.

36. The method of claim 1, comprising configuring said mobile terminal to permit said medical provider to synchronize the records on said mobile terminal with a database.

37. The method of claim 1, comprising configuring said mobile terminal to display on said display screen hospital census services.

38. The method of claim 1, wherein said ergonomic actuator comprises a thermometer icon, and said thermometer icon relates to said patient's vital statistics.

39. The method of claim 1, comprising configuring said mobile device to automatically reproduce on said display screen information from a prior time period.

40. The method of claim 1, comprising configuring said mobile device to permit said medical provider to enter a specialty area into said mobile device.

41. The method of claim 40, comprising configuring said mobile device to display on said display screen advertising targeted to said specialty area.

42. A method of presenting medical records for use by a medical provider, comprising:

formatting medical records for electronic presentation on a display screen of a mobile terminal, wherein formatting said medical records comprises providing ergonomic actuators, electronically displayed on the display screen of the mobile terminal within said medical records, to move between different screens containing different classes of medical information regarding an associated patient, wherein each ergonomic actuator is large enough to allow actuation via a user's finger; and further wherein activation of at least one of the ergonomic actuators causes automatic search, retrieval and display of medical reference information from a resource inferred and selected based on a type of patient test data associated with a prior user command most recently received at the mobile terminal.

43. The method of claim 1, wherein one of the ergonomic actuators provides access to a search engine that searches one or more medical reference databases.

44. The method of claim 7, wherein one of the ergonomic features generates a customizable information screen that permits a medical provider to customize medical test results that are electronically displayed on the display screen.

45. The method of claim 15, wherein one of the ergonomic icons generates a customizable information screen that permits a medical provider to customize medical test results that are electronically displayed on the display screen.

46. The system of claim 18, wherein one of the ergonomic icons provides access to a search engine that searches one or more medical reference databases.

47. The method of claim 19, wherein one of the ergonomic actuators generates a customizable information screen that permits a medical provider to customize medical test results that are electronically displayed on the display screen.

48. The method of claim 24, wherein one of the ergonomic actuators provides access to a search engine that searches one or more medical reference databases.

49. The method of claim 26, wherein the means generates a customizable information screen that permits a medical provider to customize medical test results that are electronically displayed on the display screen.

* * * * *

UNITED STATES PATENT AND TRADEMARK OFFICE
CERTIFICATE OF CORRECTION

| | | |
|---|---|---|
| PATENT NO. | : 7,831,449 B2 | Page 1 of 1 |
| APPLICATION NO. | : 09/776484 | |
| DATED | : November 9, 2010 | |
| INVENTOR(S) | : Ying et al. | |

It is certified that error appears in the above-identified patent and that said Letters Patent is hereby corrected as shown below:

Title page,

Item (73) Assignee: "Thompson Reuters (Healthcare) Inc." is replaced with

--Thomson Reuters (Healthcare) Inc.--

Signed and Sealed this
Thirtieth Day of August, 2011

David J. Kappos
*Director of the United States Patent and Trademark Office*